(12) United States Patent
Goebel

(10) Patent No.: US 8,070,717 B2
(45) Date of Patent: Dec. 6, 2011

(54) BLADDER CATHETER

(75) Inventor: Fred Goebel, Wilhelmsfeld (DE)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 930 days.

(21) Appl. No.: 10/496,739

(22) PCT Filed: Nov. 25, 2002

(86) PCT No.: PCT/EP02/13211
§ 371 (c)(1),
(2), (4) Date: Oct. 20, 2004

(87) PCT Pub. No.: WO03/045847
PCT Pub. Date: Jun. 5, 2003

(65) Prior Publication Data
US 2005/0065468 A1    Mar. 24, 2005

(30) Foreign Application Priority Data

Nov. 27, 2001 (DE) .................................. 101 58 091
Nov. 25, 2002 (DE) .................................. 102 55 065

(51) Int. Cl.
*A61M 29/00* (2006.01)
(52) U.S. Cl. ..................................... 604/96.01; 604/544

(58) Field of Classification Search ............... 604/93.01, 604/96.01, 540, 544, 103.06, 103, 915–917, 604/103.7; 606/191–192
See application file for complete search history.

(56) References Cited

U.S. PATENT DOCUMENTS

| | | | | |
|---|---|---|---|---|
| 5,324,260 A | * | 6/1994 | O'Neill et al. | 604/103.08 |
| 5,417,657 A | * | 5/1995 | Hauer | 604/103.02 |
| 5,496,311 A | * | 3/1996 | Abele et al. | 606/28 |
| 5,728,063 A | * | 3/1998 | Preissman et al. | 604/103.09 |
| 6,048,356 A | * | 4/2000 | Ravenscroft et al. | 606/194 |
| 2002/0082556 A1 | * | 6/2002 | Cioanta et al. | 604/113 |

FOREIGN PATENT DOCUMENTS

| | | |
|---|---|---|
| EP | 0935977 | 8/1999 |
| WO | 9725093 | 7/1997 |
| WO | 0035358 | 6/2000 |

* cited by examiner

*Primary Examiner* — Quynh-Nhu H Vu
(74) *Attorney, Agent, or Firm* — Dority & Manning, P.A.

(57) ABSTRACT

A bladder catheter for transurethral introduction into the urinary bladder by the urethrae, includes an elastic catheter shank with a fillable balloon element secured thereto and connected to a filling channel incorporated into the wall of the catheter shank. The balloon element and the catheter shank are made of polyurethane, a polyurethane-polyvinylchloride mixture or similar polyurethane-based material.

41 Claims, 4 Drawing Sheets

BLADDER CATHETER

FIELD OF THE INVENTION

The present invention is directed to a bladder catheter for transurethral introduction into the urinary bladder through the urethra, composed of a flexible catheter shaft having a refillable balloon element secured thereto, which communicates with a filling channel integrated in the wall of the catheter shaft.

BACKGROUND

When providing health care, the use of bladder catheters is often required. Bladder catheters in use today are composed of a flexible catheter shaft, to whose distal end, which is placed in the urinary bladder, a fluid-refillable balloon element is fastened. The catheter shaft has a filling channel, which leads into the balloon interior via an opening in the catheter wall. The main purpose of the balloon element is to securely mechanically anchor the catheter in the urinary bladder. In addition, when placed in the opening of the bladder, the balloon has a certain sealing function and prevents urine from flowing out of the bladder, past the catheter and through the urethra.

In the unfilled state, the balloon element resembles a sleeve pulled over the catheter shaft, fitting on the shaft all-around, typically under slight tensioning, in any case, however, in a fold-free manner. The sleeve is comparable to a hose fitting, and is usually fabricated from the same material or a substantially identical material as the shaft, but is modified in its elongation properties. Conventional balloon elements are designed with this specific type of construction, which, in the emptied state, fits closely on the shaft, to enable the balloon element to be advanced with as little as possible resistance, through the urethra into the bladder lumen. In this way, painful irritations or lesions of the urethra's mucous membrane, caused by folds or bulges in the wall of the balloon element that previously existed or formed during the advancing motion, are avoided when inserting the catheter. Once the balloon element is securely introduced into the bladder, the sleeve (balloon element) closely fitting on the shaft, is elastically expanded into a balloon by a fluid, under relatively high pressure. The material typically selected for the catheter shaft and the balloon element of conventional catheters, latex or silicon, permits an elastic expansion of the balloon element to a volume of 5 and 30 ml, respectively. These are the two standard balloon volumes for bladder catheters used in clinical practice.

Ideally, the balloon element, that has been elastically expanded into a balloon, fully retracts, even after a longer-term use of the catheter, and closely fits on the catheter shaft as a sleeve-type hose fitting, without forming folds or bulges. In this way, the drained balloon element does not cause any painful irritation or trauma to the sensitive urethra epithelium even during removal of the catheter. Typically, however, the balloon element, that has been elastically expanded for an extended period of time into a balloon, is not able to be fully elastically retracted onto the shaft. The partial loss of the sleeve elasticity caused by an elastic expansion of the balloon element over several days can be accelerated by the action of chemically aggressive urinary components (e.g., uric acid). In the case of latex-based catheters, given a long-period use, the urine regularly leads to a pronounced stiffening of the balloon element, but also to a considerable loss of elasticity of the catheter shaft. Once drained, balloon elements of the known type of construction, having a latex- or silicon-based sleeve, often exhibit residual, coarse folds or bulges in the (not fully) retracting envelope, and pose a considerable risk of injury to the patient.

Moreover, catheter materials customarily used up to now (latex, silicon, or latex- or silicon-based materials, and/or composite materials made of latex and silicon) have other clinically relevant disadvantages.

One drawback (particularly when latex materials are used) is that the balloon element does not always open out symmetrically with respect to form when elastically expanding and can burst in response to slight lateral weighting. The stability of the balloon anchoring in the opening of the bladder can be adversely affected by a pronounced asymmetry of the balloon with respect to form. Moreover, a pronounced asymmetry of the filled balloon element, depending on its placement in the opening of the bladder, can cause the catheter lumen to snap off.

A further disadvantage is that the balloon element of catheters of a conventional type of construction, as necessitated by the particularities of the manufacturing and the material, must remain below specific wall thicknesses. The minimum wall thickness of the elastically expanding sleeve, when filled to form the balloon, must be such that it is able to avoid, with certainty, falling below a lower, critical minimum wall thickness, below which the danger of rupture exists, in response to increasing shaping-out of the balloon (and the reduction in the balloon wall thickness accompanying the elastic expansion). The minimum wall thickness of the balloon element that fits on the shaft in the manner of a sleeve is typically within the range of at least 100 micrometers and requires relatively high pressures when the sleeve undergoes elastic expansion or deformation. During expansion, the balloon element assumes a shape predominantly in the radial, but also in the longitudinal direction (elongation). With increasing filling volume, the pressures forming in response to the predominantly radial elastic expansion of the balloon envelope in many cases cause a compression or stenosis of the drainage lumen of the catheter. This lumen-narrowing effect is furthered by the likewise occurring elastic expansion of the balloon in the longitudinal direction and, as a consequence thereof, the elongation of the catheter shaft in the balloon region. Both elongation components can lead to a considerable narrowing or stenosis of the catheter lumen.

It is a complex process to manufacture conventional bladder catheters, and one that requires many individual steps. In many cases, the particular dipping or molding processes do not ensure a satisfactory surface quality of the catheter and balloon. Above all, the silicon processing yields slightly rough and irregular boundary surfaces. This promotes the incrustation of urinary components, as well as the bacterial colonization of catheter surfaces.

The particular difficulty also arises when silicon is used, of water substantially permeating through the balloon envelope. To ensure that the balloon is adequately filled, it must typically be refilled in an almost daily cycle.

SUMMARY OF THE INVENTION

An object of the present invention is to provide a bladder catheter which will be able to be simply manufactured from a standpoint of production engineering and, which will benefit the patient over long-term catheter use, and which avoids disadvantages of known catheters.

The present invention provides a bladder catheter for transurethral introduction into a urinary bladder that includes a flexible catheter shaft having a wall; a filling channel integrated into the wall; and a balloon element, wherein the balloon element and the catheter shaft are made of a polyurethane-based material, such as a polyurethane, a polyurethane-polyvinyl chloride blend, or of a comparable, polyurethane-based material. It is, in fact, already known to manufacture a polyurethane shaft using the extrusion method for bladder catheters, and the method has been tried and tested in clinical applications on patients. However, due to its inadequate elongation properties, polyurethane was considered unsuitable for balloon elements of conventional design types.

For that reason, catheters having a polyurethane shaft were provided in known methods heretofore with balloon elements of latex or silicon or of related, similarly volume-expandable materials. A polyurethane sleeve that is pulled over the shaft (typical shaft diameter of approximately 4 to 6 mm for adults) and fits closely thereon, could only be elastically expanded to a balloon of a sufficient size (filling volume 5 or 30 ml) under very high pressure, which was only be able to be conditionally produced by the user using conventional means. The stresses produced in the wall of the balloon being shaped out would be considerable in any case. The drainage lumen of the catheter would be substantially constricted by the immense balloon filling pressure, as previously described.

Surprisingly, it turns out, however, that a polyurethane balloon element may nevertheless be used when manufacturing a bladder catheter, particularly when the balloon element is preformed into a balloon, as a balloon film having a wall thickness of 5 to 20 micrometers, preferably 5 to 15 micrometers. The preferably partially preformed base-state balloon in accordance with the present invention fits closely on the shaft wall in the empteied state, its envelope being folded. The preformed base-state balloon is provided in a generally known manner with two shaft pieces via which it is fastened to the catheter shaft. There is no need in accordance with the present invention to reduce the shaft diameter which allows for the base-state balloon that sits or lays folded on the shaft. The user may select the shaft thickness of the catheter in the usual manner and without any restrictions.

To conform to the catheter types in use today, the present invention proposes two basic, partially preformed, so-called base-state balloon types, which, in the completely filled, fully formed state (working balloon) have a filling volume of 5 ml or 30 ml.

To be able to achieve a working filling volume of 5 ml using filling pressure values that do not compromise the catheter shaft, the base-state balloon is designed in such a way that, in the unexpanded at-rest or base state, i.e., when the balloon is filled to the freely unfolded at-rest or base-state form (preferably spherical or spindle form), it has an at-rest or base-state volume of approximately 1.2 to 2.5 ml. In this filled base state, the cuff envelope is still unexpanded.

The balloon is preferably fastened to the shaft in the longitudinally extended form. In the process, the shaft pieces of the balloon are fixed to the shaft in such a way that they are maximally spaced apart, while avoiding a tensile stretching of the balloon envelope. The balloon envelope orients itself in a shaft-parallel lengthwise fold formation, and clings closely to the catheter shaft. The remaining at-rest filling volume in the balloon fastened in this manner, is typically less than 0.05 ml, preferably within the range of only 0.01 to 0.03 ml.

In the case of the specific embodiment of the 5 ml working filling volume, the wall thickness of the balloon envelope is preferably within the range of from 5 to 10 micrometers.

Given a larger working filling volume of, for example, 30 ml, in the unexpanded base state, i.e., when filling the balloon to the freely unfolded at-rest form (preferably cylindrical or spherical form), the base-state balloon receives a volume at rest of approximately 4 to 10 ml. The balloon is preferably fastened to the shaft in the longitudinally extended form (in the manner corresponding to the 5 ml balloon). The at-rest volume of the cuff applied in this manner is typically less than 0.08 ml, preferably in the range from only 0.02 to 0.04 ml. In the case of the specific embodiment of the 30 ml working filling volume, the wall thickness of the balloon envelope is preferably within the range of from 5 to 15 micrometers.

The polyurethane polymer used, the uninflated volume of the base-state balloon, and the wall thickness of the balloon are selected in such a way that the safety range of volumetric expandability of the balloon is preferably 300 to 400 percent and does not exceed a safety range of from 400 to 450 percent.

The balloon envelope that forms longitudinal or also unaligned folds allows a partially preformed base-state balloon to be elastically expanded to the filled working balloon in that comfortable pressure values are applied which do not constrict the catheter lumen. In the case of the preformed balloon according to the present invention, the filling pressure is typically only 50-200 mbar (given 5 ml working volume) and 50-250 mbar (given 30 ml working volume), respectively.

For the balloon according to the present invention, Pellethane 2363 materials having a Shore hardness of 70 to 90 along with their respective subforms (A,AE) are preferably used. Materials of other manufacturers having comparable technical material data may be used correspondingly.

The balloon, together with its shaft pieces, is bonded or fused to the catheter shaft. In the manufacturing of the base-state balloon, the transition regions from the shaft pieces to the central, mid-position diameter of the base-state balloon are designed to have wall thicknesses which continuously decrease from the shaft piece to the central, mid-position diameter.

It is advantageous when, after joining the balloon to the catheter shaft, the end rims of the shaft pieces are smoothed, for example, by the action of heat or application of solvents, so that no sharp-edged transitions are present in the transition region from the shaft to the balloon.

In addition, when polyurethane is used for the catheter shaft, the wall thickness of the catheter shaft is advantageously smaller than in previous designs, enabling the catheter drainage lumen to be enlarged, given the same external diameter. Thus, given a favorable material selection, a shaft wall thickness of from 0.4 to 0.8 mm, preferably from 0.4 to 0.6 mm suffices. The catheter shaft nevertheless retains its rigidity or safety against buckling, as required for insertion into the urethra in patient applications. To further reduce the catheter wall thickness, the catheter shaft is preferably formed from two concentrically extruded tubes, the inner tube preferably being designed to be thinner and harder than the outer tube (co-extrusion). To achieve the same objective, a spiral reinforcement or a stabilizing mesh worked into the shaft are also conceivable.

Moreover, the surfaces of both the balloon preferably fabricated using the blow-molding method and, respectively, of the preferably extruded shaft are of highest quality when polyurethane is used. Incrustation by urinary components, as well as bacterial colonization are rendered difficult by the special surface evenness.

The catheter described in accordance with the present invention is simple to manufacture in terms of production engineering and eliminates the need for cost-intensive manufacturing steps in comparison to conventional catheter types, such as, above all, latex catheters manufactured using the dipping method.

The catheter shaft is preferably provided with a plurality of filling openings in the region covered by the balloon. These filling openings have a square, preferably rectangular shape.

This substantially prevents the thin film of the balloon from being able to close this opening or these openings in the manner of a valve and thereby complicate the process of emptying the balloon.

The dimensional design of the base-state balloon is calculated, i.e., its wall thickness is selected in a way that allows the envelope to be elastically expanded up to the working volume, while avoiding a non-elastic overstretching, i.e., the elasticity of the ballon material is completely retained, even in the case of long-term catheter use. Therefore, once the balloon is completely drained, it clings closely to the catheter shaft, again in longitudinal folds, as it is withdrawn through the urethra, and it is non-traumatizing.

The so-called suprapubic bladder catheter, another embodiment and version of a bladder catheter that is common in practice, may likewise be optimized by combining a polyurethane shaft with a polyurethane-based balloon element in accordance with the present invention. When the suprapubic catheter system is used, a hollow needle element is inserted through the anterior abdominal wall directly into the urinary bladder, directly above the pubic bone. The needle element may be designed as a conventional hollow needle, as a guide needle that is laterally open across the entire length of the needle (the catheter is inserted laterally into the guide needle), or, for example, as a so-called spread-type needle (the hollow needle is composed of two halves which are separable from one another by spreading).

Preformed balloon elements, in the specific embodiment according to the present invention of the balloon element having a working volume of 5 ml in the wall-thickness range of preferably 5 to 10 micrometers, may be pushed through the application needle when a lubricating agent is used, without having to restrict the diameter of the catheter shaft. Thus, the patient may also benefit from the afore-mentioned advantages of a bladder catheter that is manufactured in its entirety from polyurethane, when the suprapubic version is used.

It is also vitally important to the patient, who is typically catheterized suprapubically for extended periods of time, that the drained balloon element be removable, to the greatest possible degree without causing trauma, through the puncture channel in the bladder and abdominal wall that has already healed or granulated following a relatively long catheter application.

BRIEF DESCRIPTION OF THE DRAWINGS

The present invention is explained in greater detail on the basis of exemplary embodiments illustrated in the drawings, whose figures show.

DETAILED DESCRIPTION

Figure 1:
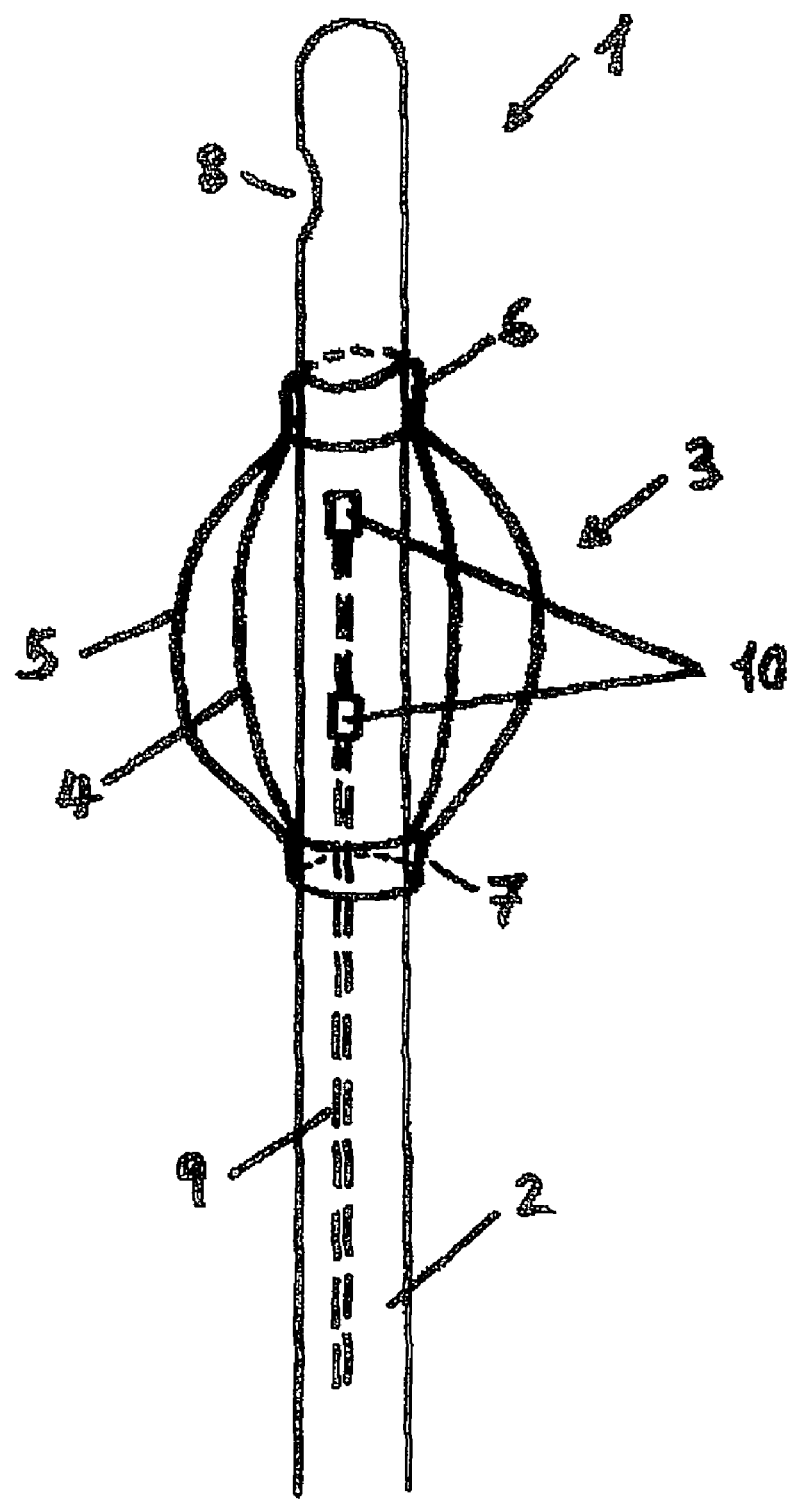
FIG. 1 a lateral, part-sectional view of the distal end of the catheter.

FIG. 1 shows the distal end of a bladder catheter 1 in a part-sectional, lateral view. Balloon element 3, which is shown in a sectional view both as base-state balloon 4 (volume at rest) and as inflated balloon 5 (working volume), is fastened to catheter shaft 2. Balloon element 3 is made of a polyurethane-based material; in its form as base-state balloon 4, it has a wall thickness of 5 to 20, preferably of 5-15 µm. It is provided with shaft pieces 6 and 7, via which it is bonded to catheter shaft 2. At its distal end, hollow catheter shaft 2 has opening 8, via which urine can flow out of the urinary bladder. A filling channel 9 situated in the wall of catheter shaft 2 leads to opening or plurality of openings 10 in catheter shaft 2, which is/are placed in the region of balloon element 3.

Once catheter 2 is introduced into the urinary bladder through the urethra, a suitable fluid, directed through channel 9 and opening(s) 10 into balloon element 3, fills balloon element 3, i.e., elastically expands it as it is increasingly filled from the base-state volume to its working volume.

Figure 2:
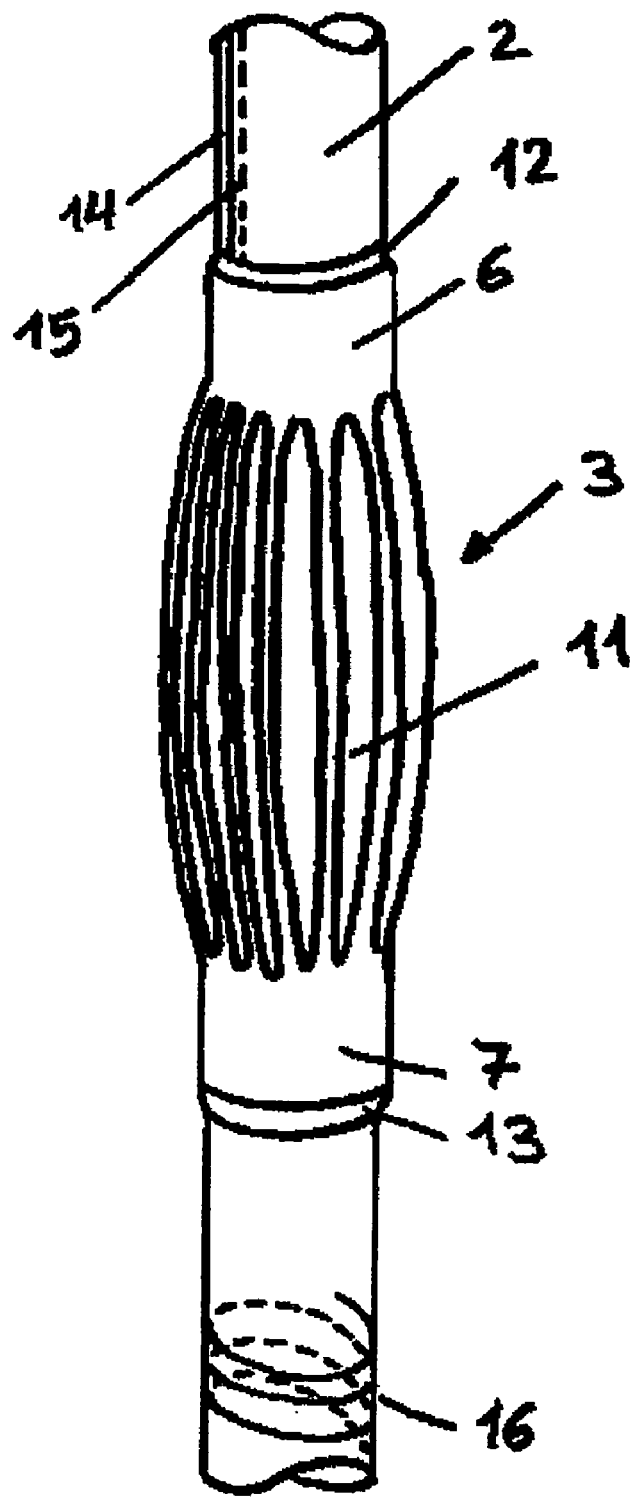
FIG. 2 a lateral view of the catheter prior to its insertion.
Figure 3:
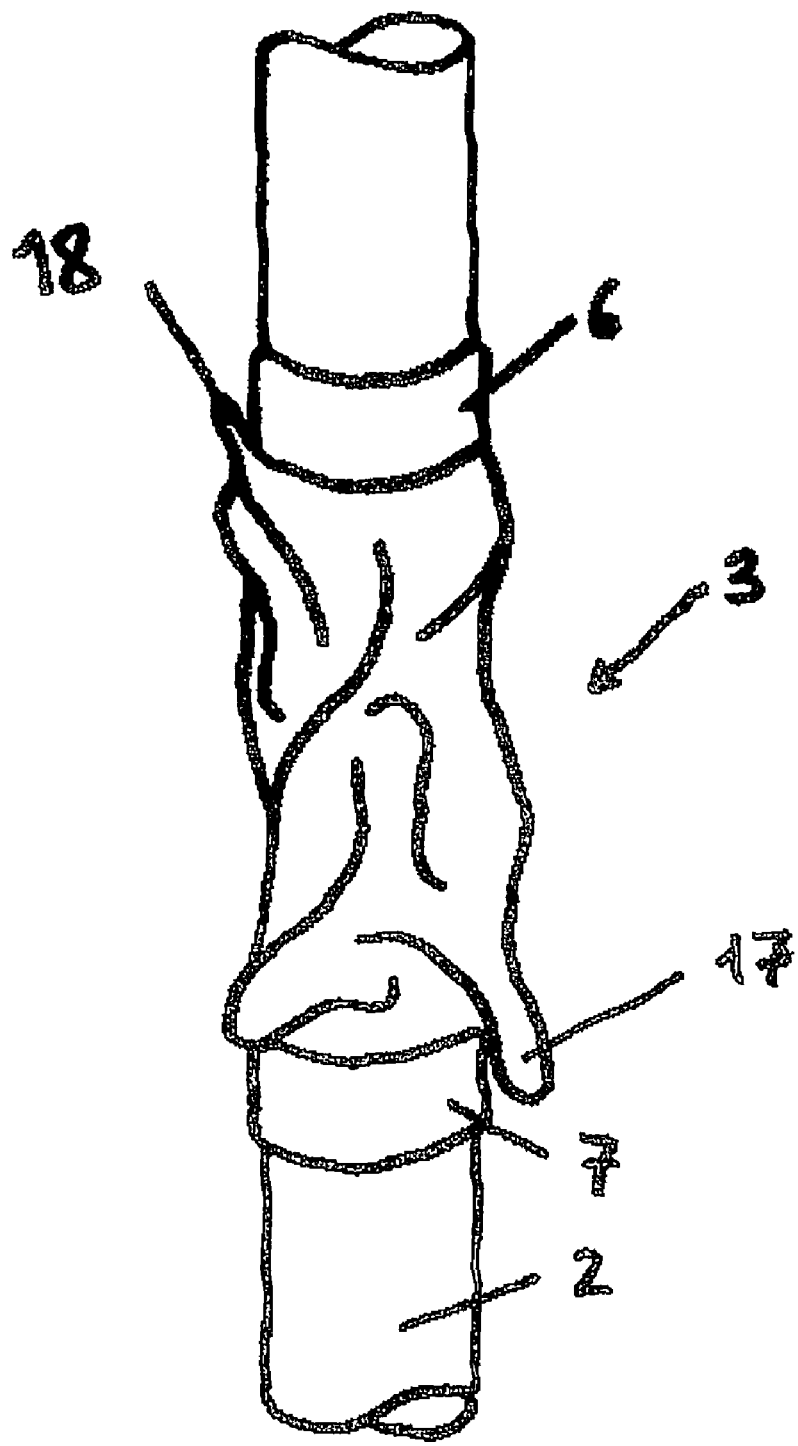
FIG. 3 a lateral view of the catheter prior to its introduction into or withdrawal from the urethra.

In its completely emptied state, balloon element 3 fits on the surface of shaft 2, as shown in FIGS. 2 and 3.

In FIG. 2, balloon element 3 shapes itself into a fold formation 11 that runs in the longitudinal direction of catheter shaft 2. Fold formation 11 substantially extends between the two shaft pieces 6 and 7.

The fold formation permits a bulging of balloon element 3, which leads to base-state balloon 4 shown in FIG. 1. This bulging takes place without any appreciable pressure and may vary in magnitude depending on the material used. In the unexpanded, freely unfolded state, base-state balloon 4 contains a volume at rest which is clearly less than the filling volume contained in filled balloon 5 (working volume). To illustrate the present invention, base-state balloon 4 is sketched having a relatively large volume at rest in FIG. 1. To reduce the overall space required by the fold formation to the greatest degree possible, base-state balloon is mounted on the shaft in the longitudinally oriented form. The shaft pieces of the balloon are spaced as far apart as possible, as shown in FIG. 2, without thereby tensioning the balloon envelope.

Figure 4:
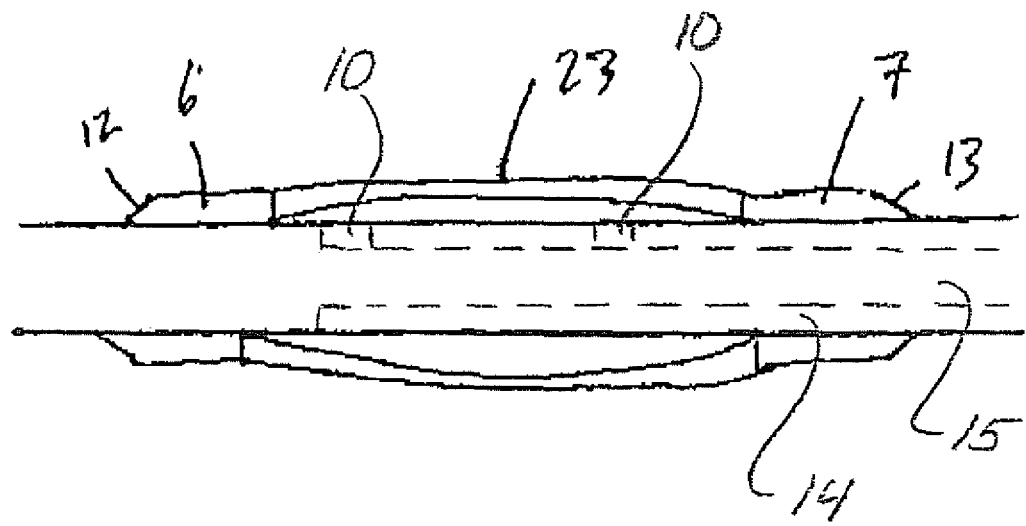
FIG. 4 shows a schematic view of the transition region from the shaft pieces to a central midposition in cross-section.

As shown in FIG. 4, the transition region from shaft pieces 6 and 7 to the central, mid-position section 23 of balloon 3 is kept as a continuous, fluid transition, so that the wall thicknesses continuously decrease from the thickness at shaft pieces 6 and 7 to the thickness at the central, mid-position diameter of base-state balloon 4. As shown in FIGS. 2 and 4, end rims 12 and 13 of shaft pieces 6 and 7 are smoothed, so that there is no sharp-edged transition.

As indicated in the upper portion of FIG. 2, catheter shaft 2 may be composed of two preferably co-extruded tubes 14 and 15, which fit one inside the other.

The lower portion of FIG. 2 shows the option of providing catheter shaft 2 with a spiral reinforcement 16 of metal.

FIG. 3 shows one specific embodiment of balloon element 3, where base-state balloon 4 is fastened to the shaft in such a way that it is not aligned in a fold formation, but folded randomly or unsystematically. Thus, the shaft pieces of the balloon are not maximally spaced apart, but to a lesser degree.

The fold formation may run in any way at all, thus, for example, also transversely or at right angles to the catheter axis. However, since the balloon wall is exceptionally thin, once the balloon is drained, it may cling very closely to the surface of catheter shaft 2. In some instances, hanging sack-like folds 17 or 18 form at shaft pieces 6 or 7 when the catheter is inserted or removed. On the right side of FIG. 3, 17 denotes a hanging sack-like fold which forms during insertion of the catheter, and on the left side of the figure, 18 denotes a hanging sack-like fold which forms during removal of the catheter through the urethra. However, in the wall-thickness range named in accordance with the present invention, even such hanging sack-like folds have no disadvantageous effect during passage of the balloon element through the urethra.

What is claimed is:

1. A bladder catheter for transurethral or suprapubic introduction into a urinary bladder comprising:
    a flexible catheter shaft having a wall;

a filling channel defined in the catheter shaft; and a balloon element made of a polyurethane-based material having a Shore hardness of 70 to 90 and fastened to the catheter shaft, the balloon element having a wall thickness of 5 to 20 micrometers and a preformed blow-molded shape, wherein in a first empty and unrestrained base state, the balloon element is fitted over the catheter shaft with folds and has a first empty volume, in a second state the balloon element is filled and unfolded without elastic expansion to a second fill volume greater than the first empty volume, and in a third fully formed state, the balloon element has an elastic expansion to a third fill volume that is at least about double the second fill volume.

2. The bladder catheter as recited in claim 1, wherein the polyurethane-based material includes at least one of a polyurethane and a polyurethane-polyvinyl chloride blend.

3. The bladder catheter as recited in claim 1, wherein the wall thickness is 5 to 15 micrometers.

4. The bladder catheter as recited in claim 1, wherein the balloon element in the first base state includes a plurality of longitudinally oriented folds, the balloon element clinging to the catheter shaft in the folded state.

5. The bladder catheter as recited in claim 1, wherein the balloon element in the third fully formed state has a third fill volume of about 5 ml.

6. The bladder catheter as recited in claim 5, wherein the balloon element in the second filled state has a second fill volume of 1.2 to 2.5 ml.

7. The bladder catheter as recited in claim 6, wherein the balloon element has an empty volume of 0.01 to 0.03 ml in the first base folded state.

8. The bladder catheter as recited in claim 1, wherein the balloon element has at least one of a spherical and a spindle form.

9. The bladder catheter as recited in claim 1, wherein the balloon element has a third fill volume in the third fully formed state of about 30 ml.

10. The bladder catheter as recited in claim 9, wherein the balloon element in the second filled state has a second fill volume of 4 to 12 ml.

11. The bladder catheter as recited in claim 9, wherein the balloon element fits on the shaft and includes a plurality of longitudinal folds in the first base folded state.

12. The bladder catheter as recited in claim 11, wherein the balloon element has an at-rest volume of less than 0.08 ml in the first base folded state.

13. The bladder catheter as recited in claim 11, wherein the balloon element has a first empty volume of 0.01 to 0.03 ml in the folded state.

14. The bladder catheter as recited in claim 1, wherein the balloon element includes a fold formation aligned in parallel with the catheter shaft and wherein the balloon element is joined to the catheter shaft without stretching the balloon element.

15. The bladder catheter as recited in claim 1, wherein the balloon element includes shaft pieces fastenable to the catheter shaft, a center section and a transition region between the center section and the shaft pieces, and wherein a wall thickness of the balloon element continuously decreases from the shaft pieces to the center section.

16. The bladder catheter as recited in claim 15, wherein at least one shaft piece includes a smoothed end rim.

17. The bladder catheter as recited in claim 1, wherein catheter shaft includes an outer tube and an inner tube disposed inside the outer tube.

18. The bladder catheter as recited in claim 17, wherein the inner tube is co-extruded with the outer tube.

19. The bladder catheter as recited in claim 17, wherein the inner tube is made of a harder material than the outer tube.

20. The bladder catheter as recited in claim 1, wherein the catheter shaft includes at least one filling opening in a region of the balloon element.

21. The bladder catheter as recited in claim 20, wherein the at least one filling opening has at least one of a square and a rectangular shape.

22. The bladder catheter as recited in claim 1, wherein the catheter shaft has a spiral reinforcement of metal.

23. The bladder catheter as recited in claim 1, wherein the catheter shaft is an extruded shaft.

24. The bladder catheter as recited in claim 1, wherein the balloon element has a safety range of volumetric expandability of 400 to 450 percent.

25. The bladder catheter as recited in claim 1, wherein the balloon element has a safety range of volumetric expandability of 300 to 400 percent.

26. The bladder catheter as recited in claim 1, wherein the balloon element has a third fill volume of about 5 ml and a filling pressure of 50 to 200 millibar in the third fully formed.

27. The bladder catheter as recited in claim 1, wherein the balloon element has a volume of about 30 ml and a filling pressure of 50 to 200 millibar in the third fully formed state.

28. The bladder catheter as recited in claim 1, wherein the catheter is for long-term use.

29. The bladder catheter as recited in claim 1 wherein the balloon element in the folded state has randomly distributed folds.

30. The bladder catheter as recited in claim 1 wherein the balloon element in the folded state has hanging sack folds.

31. The bladder catheter as recited in claim 1 wherein the balloon element in the folded state clings to the catheter shaft.

32. The bladder catheter as recited in claim 1 wherein the balloon element includes shaft pieces fastenable to the catheter shaft.

33. The bladder catheter as recited in claim 1 wherein the catheter shaft is made of a polyurethane-based material.

34. The bladder catheter as recited in claim 1 wherein the bladder catheter is for transuretheral introduction.

35. A method for manufacturing the bladder catheter as recited in claim 1, comprising blow-molding the polyurethane-based material having a Shore hardness of 70 to 90 into the preformed shape of the balloon element having a wall thickness of 5 to 20 micrometers.

36. A bladder catheter for transurethral or suprapubic introduction into a urinary bladder comprising:

a flexible catheter shaft having a wall;

a filling channel integrated into the wall; and a balloon element connected to the catheter shaft, the balloon element being made of a polyurethane-based material having a Shore hardness of 70 to 90, the balloon element being fillable from a folded state to a filled state, the balloon element in the folded state disposed around the catheter shaft with unrestrained hanging sack folds.

37. A method for manufacturing the bladder catheter as recited in claim 36, comprising blow-molding the polyurethane-based material having a Shore hardness of 70 to 90 into a preformed shape of the balloon element having a wall thickness of 5 to 20 micrometers.

38. A bladder catheter for transurethral or suprapubic introduction into a urinary bladder comprising:

a flexible catheter shaft having a wall;

a filling channel integrated into the wall; and a balloon element connected to the catheter shaft, the balloon element is made of a polyurethane-based material having a Shore hardness of 70 to 90, wherein the balloon element is fillable from a folded state to a filled state, the balloon element in the folded state disposed around the catheter shaft with randomly distributed unrestrained folds.

39. The bladder catheter as recited in claim 38 wherein the catheter shaft is made of a polyurethane-based material.

40. The bladder catheter as recited in claim 38 wherein the bladder catheter is for transuretheral introduction.

41. A method for manufacturing the bladder catheter as recited in claim 38, comprising blow-molding the polyurethane-based material having a Shore hardness of 70 to 90 into a balloon element having a preformed shape and a wall thickness of 5 to 20 micrometers.

* * * * *